(12) United States Patent
Kim et al.

(10) Patent No.: US 6,800,380 B2
(45) Date of Patent: Oct. 5, 2004

(54) ORGANOMETALLIC LUMINESCENT MATERIALS AND ORGANIC ELECTROLUMINESCENT DEVICE CONTAINING SAME

(75) Inventors: Youngkyoo Kim, Pusan (KR); Jae-Gyoung Lee, Seongnam-shi (KR)

(73) Assignee: Nessdisplay Co., Ltd., Suwon-si (KR)

( * ) Notice: Subject to any disclaimer, the term of this patent is extended or adjusted under 35 U.S.C. 154(b) by 44 days.

(21) Appl. No.: 09/992,409

(22) Filed: Nov. 26, 2001

(65) Prior Publication Data

US 2003/0165711 A1 Sep. 4, 2003

Related U.S. Application Data

(63) Continuation-in-part of application No. 09/336,713, filed on Jun. 21, 1999, now abandoned.

(30) Foreign Application Priority Data

Jun. 23, 1998 (KR) ............................................. 98-23645

(51) Int. Cl.[7] .................. C07D 293/00; H05B 33/14
(52) U.S. Cl. ................ 428/690; 548/100; 548/101; 548/107; 548/108; 548/110; 548/120; 548/148; 548/160; 548/217; 548/224; 548/235; 549/3; 549/4; 549/31; 549/32; 428/917; 428/704; 313/504; 313/506; 252/301.16; 252/301.21
(58) Field of Search .............................. 548/100–101, 548/107–108, 110, 120, 148, 160, 217, 224, 235; 549/3–4, 31–32; 428/917, 690, 704; 313/504, 506

(56) References Cited

U.S. PATENT DOCUMENTS 5,755,999 A * 5/1998 Shi et al. ............... 252/301.16
6,083,634 A * 7/2000 Shi ......................... 428/690

FOREIGN PATENT DOCUMENTS

JP 10-140145 * 5/1998 ........... C09K/11/06

\* cited by examiner

*Primary Examiner*—Deborah Jones
*Assistant Examiner*—Ling Xu
(74) *Attorney, Agent, or Firm*—Jacobson Holman PLLC

(57) ABSTRACT

An organometallic luminescent material comprising the compound of formula (I) of the present invention can emit pure blue light and have high thermal stability:

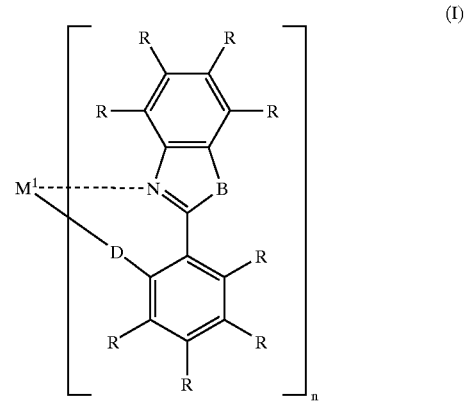

wherein, $M^1$ is a monovalent or tetravalent metal selected from the group consisting of Li, Na, K, Zr, Si, Ti, Sn, Cs, Fr, Rb, Hf, Pr, Pa, Ge, Pb, Tm and Md;

R is hydrogen or $C_{1-10}$ alkyl;

B is O, S, Se or Te;

D is O or S; and n is an integer ranging from 1 to 4.

6 Claims, 5 Drawing Sheets

OELD-B1

OELD-B2

OELD-B3

ORGANOMETALLIC LUMINESCENT MATERIALS AND ORGANIC ELECTROLUMINESCENT DEVICE CONTAINING SAME

CROSS-REFERENCE TO RELATED APPLICATION

This application is a continuation-in-part of U.S. patent application Ser. No. 09/336,713, filed on Jun. 21, 1999, now abandoned.

FIELD OF THE INVENTION

The present invention is directed to a novel organometallic luminescent material, and more particularly, to a novel organometallic luminescent material having the capability of emitting pure blue light and high thermal stability, and an organic electroluminescent device (OELD) containing same.

BACKGROUND OF THE INVENTION

Conventional organometallic luminescent compounds used in organic electroluminescent devices are mostly complexes of divalent or trivalent metals such as zinc and aluminum.

For example, U.S. Pat. No. 5,456,988 describes 8-hydroxyquinoline complexes of zinc, aluminum and magnesium as organic luminescent materials; U.S. Pat. No. 5,837,390 discloses magnesium, zinc and cadmium complexes of 2-(o-hydroxyphenylbenzoxazole); Japanese Patent Laid-Open Publication No. 07-133483 reports luminescent complexes of 2-(o-hydroxyphenylbenzoxazole) with divalent metals such as magnesium and copper; and U.S. Pat. No. 5,529,853, and Japanese Patent Laid-Open Publication Nos. 06-322362, 08-143548 and 10-072580 disclose divalent or trivalent metal complexes of 10-hydroxybenzo[10]quinoline.

The above organometallic luminescent compounds containing a divalent or trivalent metal have relatively loosely-bound ligands and an extended system of conjugation. As a result, they are relatively unstable and emit green or red light but not blue light.

Therefore, there has existed a need to develop an organometallic luminescent material having an improved stability and light emission characteristics such as the capability of emitting pure blue light.

SUMMARY OF THE INVENTION

Accordingly, it is a primary object of the present invention to provide a novel organometallic luminescent material having good stability and desired emission characteristics, and an organic luminescent device containing same.

In accordance with the present invention, there is provided an organometallic luminescent complex of formula (I).

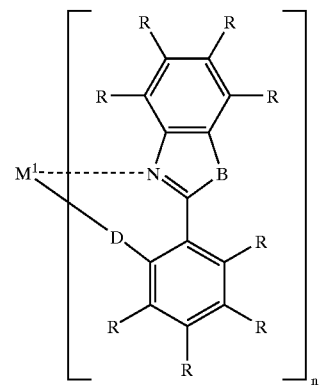

wherein,
M$^1$ is a monovalent or tetravalent metal selected from the group consisting of Li, Na, K, Zr, Si, Ti, Sn, Cs, Fr, Rb, Hf, Pr, Pa, Ge, Pb, Tm and Md;
R is hydrogen or $C_{1-10}$ alkyl;
B is O, S, Se or Te;
D is O or S; and
n is an integer ranging from 1 to 4.

BRIEF DESCRIPTION OF THE DRAWINGS

The above and other objects and features of the present invention will become apparent from the following description thereof, when taken in conjunction with the accompanying drawings wherein.

DETAILED DESCRIPTION OF THE INVENTION

The organometallic luminescent materials of the present invention include benzoxazole- or benzthiazole-metal complexes of formula (I).

Among the organometallic luminescent materials of the present invention, preferred are those listed in Table I.

TABLE I

| Compound No. | M¹ | B | D | N | R | $\gamma_{max}$ (nm) | color |
|---|---|---|---|---|---|---|---|
| 1 | Li | O | O | 1 | H | 450 | blue |
| 2 | Na | — | O | 1 | H | 455 | blue |

Compound 1,2-(2-hydroxyphenyl)benzoxazol-lithium (LiPBO) can be applied as a stable blue emission layer in an organic electroluminescent device (OELD) because it has a high glass transition temperature of more than 200° C.

The organometallic luminescent compound of the present invention may be prepared by reacting an organic compound that can serve as a ligand with an appropriate metal compound in a suitable solvent.

Exemplary solvents which can be used in the present invention include water, ethanol, methanol and propanol.

Representative metal compounds that can be used to prepare the organometallic luminescent compounds of the present invention are LiOH, NaOH, KOH, NaCl, KCl, LiCl, $ZrCl_4$, $SnCl_4$, $TiCl_4$, $SiCl_4$, $BeCl_2$, $MgCl_2$, $AlCl_3$, $CaCl_2$ and $ZnCl_2$.

Representative organic compounds which can be used as ligands in the present invention include 2-(2-hydroxyphenyl) benzoxazole and 2-(2-hydroxy-phenyl) benzthiazole.

The reaction of the organic and metal compounds to prepare the organometallic luminescent compound of the present invention may be carried out in stoichiometric amounts, which depend on n, at a temperature ranging from 25 to 100° C. for 1 to 24 hours.

The organometallic complex of the present invention can be used as a luminescent doping material as well. For example, when it is doped in an amount of about 2% in a blue light emitting luminescent layer, the emitting light changes from blue to light blue or green. Accordingly, an efficient electroluminescent device capable of emitting a tuned color can be prepared.

The organic luminescent device of the present invention comprises an organic interlayer which may be in the form of a single layer, in the form of a double layer containing a hole transporting layer (HTL) or an electron transporting layer (ETL) in addition to the light emitting luminescent layer, or in the form of a multi layer containing still additionally a hole injecting layer (HIL) or a hole blocking layer (HBL). The organometallic luminescent material of the present invention can be used alone, or in combination with a polymer or an inorganic material. Further, it may be doped in a polymer to give a fluorescent thin layer.

Figure 1A:
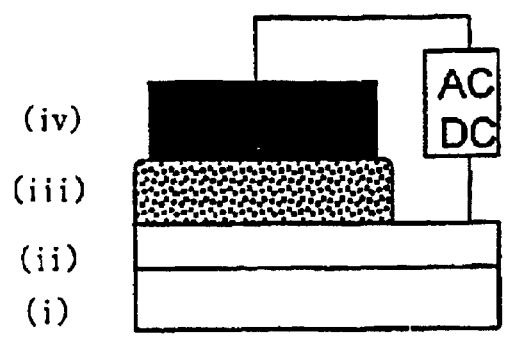
FIGS. 1a, 1b and 1c illustrate schematic diagrams of organic electroluminescent devices having single-layered, double-layered and multi-layered organic interlayers, respectively, FIG. 1d, energy band diagrams of OELDs, and FIG. 1e, chemical structures of (a) m-MTDATA, (b) NPB, (c) LiPBO, (d) BCP and (e) Alq3.
Figure 1B:
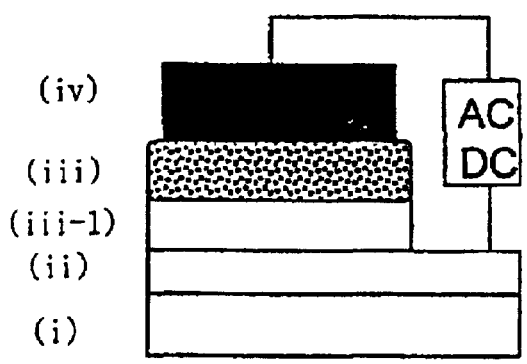
Figure 1C:
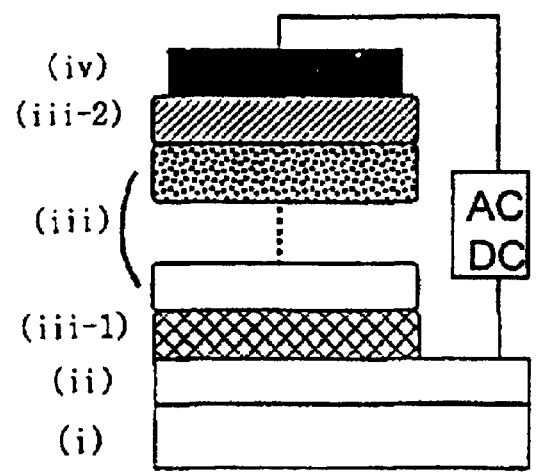

An example of the electroluminescent device of the present invention contains a single organic layer as shown in FIG. 1a. The device consists of (i) a glass substrate, (ii) a transparent ITO (indium tin oxides) anode electrode layer, (iii) an organic luminescent layer containing the organometallic luminescent material of the present invention, and (iv) a metal cathode electrode layer. Another example of the inventive device has an additional hole transporting layer (iii-1) as shown in FIG. 1b, or a multi-layered structure shown in FIG. 1C, wherein (iii-2) denotes an additional electron transporting layer. The electroluminescent device of the present invention may be operated with either direct or alternative current, while the direct current is preferred.

The organic luminescent layer of the present invention may be formed by a conventional method including a wet process such as spin coating, and a dry process such as a vapor deposition, vacuum thermal deposition, sputtering and electron beam deposition method.

The novel organometallic luminescent compound of the present invention is capable of emitting blue light, and in particular, the inventive complexes containing monovalent metals are stable even at a high temperature and emit bright blue light.

The present invention is further described and illustrated in Examples, which are however, not intended to limit the scope of the present invention.

Preparation 1: 2-(2-Hydroxyphenyl)benzoxazole-lithium (LiPBO)

2-(2-hydroxyphenyl) benzoxazole and lithium oxide were added to 250 ml of ethanol in a molar ratio of 1:1 and the mixture was refluxed at 78° C. for 4 hours. The reaction mixture was filtered and the solvent and moisture were removed under a reduced pressure to give the titled compound of formula (I-1) (compound 1).

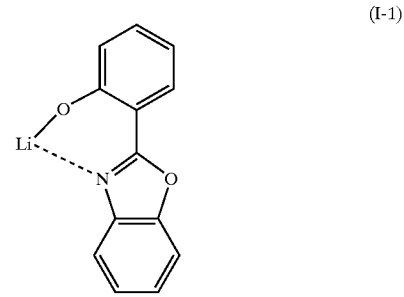

(I-1)

The compound thus obtained was analyzed by ICP-AES and EA, and the results are as follows:

Calculated=>C: 71.95, H: 3.68, N: 6.44, O: 14.73, Li: 3.20
Found=>C: 71.82, H: 3.95, N: 6.34, O: 13.94, Li: 3.95

EXAMPLE 1

Photoluminescence Spectrum and Thermal Stability of LiPBO

Figure 2:
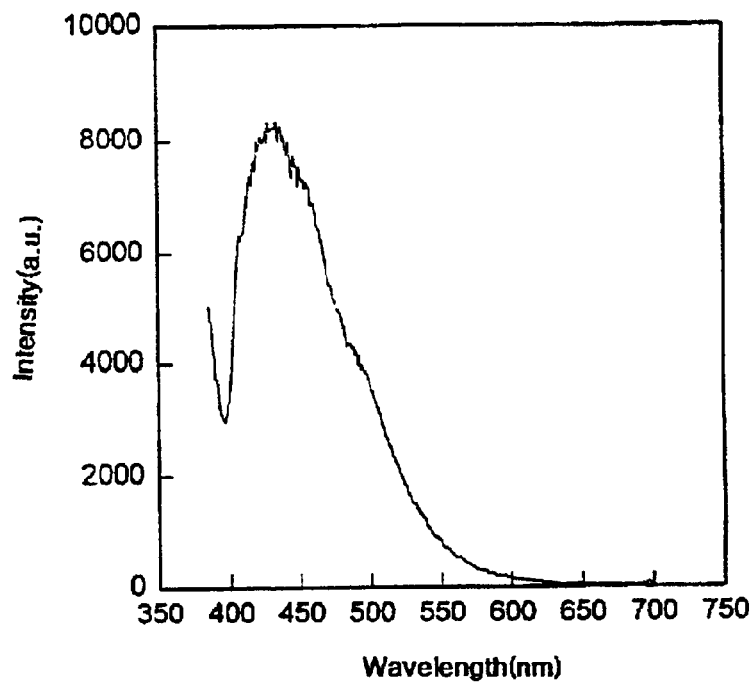
FIG. 2 shows the light emission spectrum of the organometallic luminescent material obtained in Preparation 1 of the present invention.

The light emission spectrum of the LiPBO complex thus obtained was measured and shown in FIG. 2. The photoluminescence spectrum of the purified LiPBO film shows a maximum peak at 450 nm.

Figure 3:
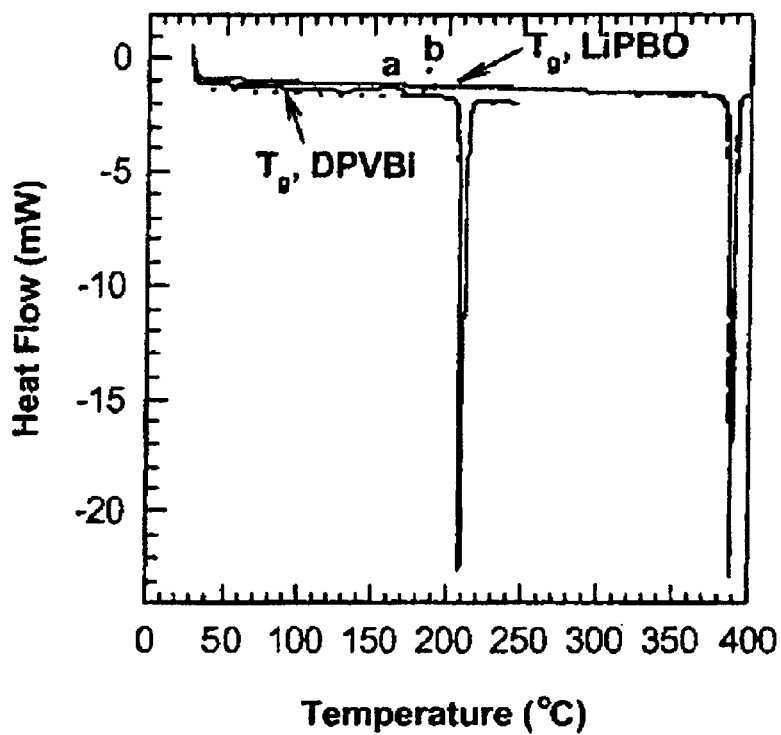
FIG. 3 represents thermal stabilities of the LiPBO obtained in Preparation 1 and a DPVBi powder.

Also, the thermal stability of the purified LiPBO was examined by using differential scanning calorimeter (DSC). A second DSC run was performed to verify the scan is reproducible after heating and cooling. For comparison, 4,4-bis(2,2-diphenylvinyl)biphenyl (DPVBi), which is known to be one of the best organic blue emitters, was also examined by DSC. The thermal relaxation behaviors of the LiPBO and a DPVBi powder are shown in FIG. 3. The glass transition temperature of the LiPBO and DPVBi were ca. 205° C. and 385° C., respectively.

Preparation 2: 2-(2-Hydroxyphenyl)-benzoxazole-sodium (NaPBO)

2-(2-hydroxyphenyl)benzoxazole and NaOH were added to 250 ml of ethanol in a molar ratio of 1:1 and the mixture was refluxed at 78° C. for 4 hours. The reaction mixture was filtered and the solvent and moisture were removed under a reduced pressure to obtain the titled compound of formula (I-2) (compound 2).

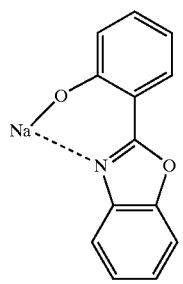

(I-2)

The maximum wavelength and emitted color of the complex thus obtained were 455 nm and blue, respectively (Table I).

The compound thus obtained was analyzed by ICP-AES and EA, and the results are as follows:
Calculated=>C: 66.96, H: 3.43, N: 6.00, O: 13.73, Na: 9.88
Found=>C: 66.41, H: 3.20, N: 6.24, O: 14.04, Na: 10.11
Preparation 3: Tetra[2-(2-hydroxyphenyl)benzoxazolato] zirconium (ZrPBO)

Preparation 1 was repeated except that zirconium chloride (ZrCl4) was used instead of lithium to give the titled compound. The compound thus obtained was analyzed by ICP-AES and EA, and the results are as follows:
Calculated=>C: 67.01, H: 3.44, N: 6.00, O: 13.75, Zr: 9.80
Found=>C: 66.79, H: 3.63, N: 5.97, O: 13.69, Zr: 9.92
Preparation 4: Double-Layered OELD Indium-tin-oxide (ITO) was coated on a glass substrate to form a transparent anode layer. The coated substrate was subjected to photolithography and the patterned ITO glass was cleaned with a solution containing a non-phosphorous detergent, acetone and ethanol.

An equal weight mixture of polyetherimide of formula (II) and triphenyldiamine of formula (III) was dissolved in chloroform to a concentration of 0.5 wt. %, and the resulting mixture was spin-coated on the ITO glass to form a hole transporting layer;

an organic luminescent layer, and then, aluminum was vapor deposited to a thickness of 500 nm to form a cathode layer on the organic luminescent layer. Subsequently, the device was packaged to obtain an organic electroluminescent device (OELD) having a double-layered structure as shown in FIG. 1b.

EXAMPLE 2

EL Spectrum of OELD

Figure 4:
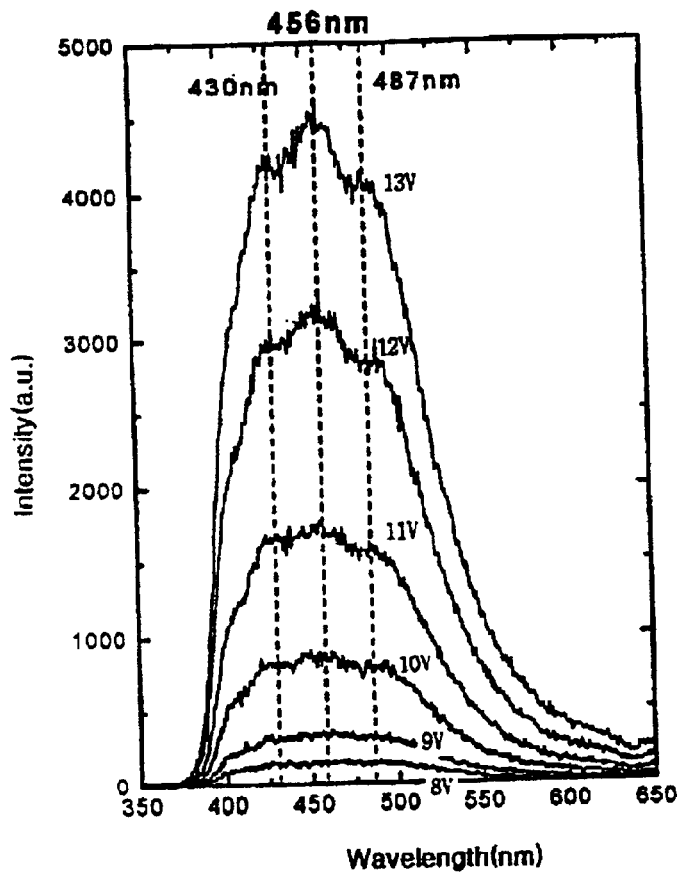
FIG. 4 exhibits the electroluminous spectra of the electroluminescent device obtained in Preparation 4 of the present invention.

FIG. 4 exhibits electroluminous spectra of the OELD obtained in Preparation 4 observed at various applied voltages of 8, 9, 10, 11, 12 and 13V. The main peak appears at 456 nm and shoulder peaks are observed at 430 and 487 nm. The emitted light was blue.
Preparation 5: Double-Layered OELD Preparation 4 was repeated except that ZrPBO with a thickness of 50 nm was used as a luminescent material and Li:Al (Li content 0.15%) was used as a cathode layer to obtain an OELD having a double layer structure. The current injection started at ca. 3.5V. 24,300 cd/m$^2$ was achieved at 11V and the current density was 4,831 A/m$^2$. The luminous efficiency was 5.03 cd/A.
Preparation 6: Multi-Layered OELD Preparation 3 was repeated except that 4,4',4"-tris(N-3-methylphenyl-N-phenylamino)triphenylamine (m-MTDATA), N,N'-diphenyl-N,N'-bis(1-naphthyl)-(1,1'-biphenyl)-4,4'-diamine (NPB) and bathocuproine (BCP) were used in forming hole injecting layer (HIL), hole transporting layer (HTL) and hole blocking layer (HBL), respectively, to prepare three types (OELD-B1, OELD-B2 and OELD-B3) each having a multi-layered structure.

OELD-B1 comprises a glass plate and layers of indium-tin oxide (ITO), 4,4',4"-tris[N-(3-methylphenyl)-N-phenylamino]triphenylamine (m-MTDATA) (200 Å), N,N'-diphenyl-N,N'-bis(1-naphthyl)-(1,1-biphenyl)-4,4'-diamine (NPB or α-NPD) (75 Å), LiPBO (200 Å), bathocuproine (BCP) (100 Å), and Li:Al (1500 Å). OELD-B2 is composed of a glass plate and layers of ITO, m-MTDATA (200 Å), NPB (100 Å), LiPBO (200 Å), tris(8-quinolinolato)

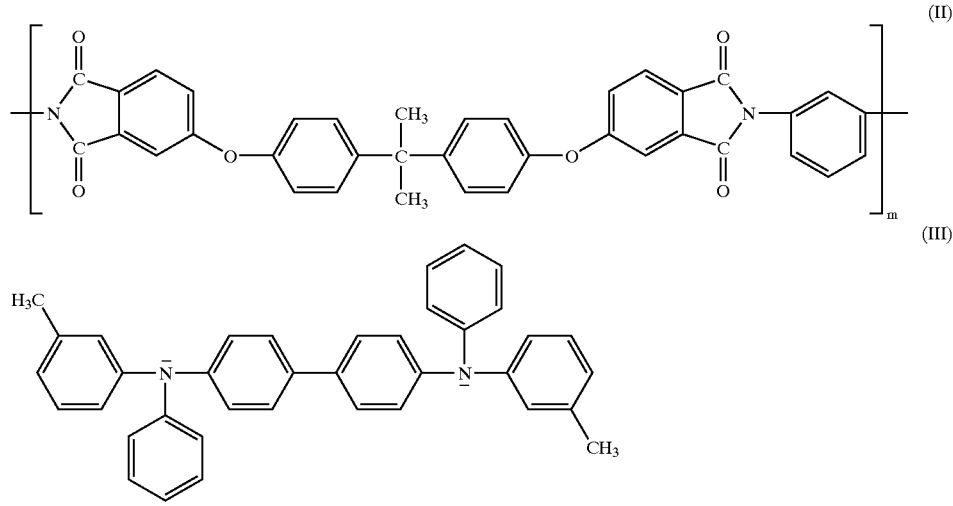

wherein m is an integer of two or higher.

On the hole transporting layer, 2-(2-hydroxyphenyl) benzoxazole-lithium (LiPBO) complex obtained in Preparation 1 was vapor deposited to a thickness of 20 nm to form aluminum (Alq3) (75 Å), and Li:Al (1500 Å). Further, OELD-B3 had the layer structure of glass/ITO/m-MTDATA (200 Å)/NPB (100Å)/LiPBO (200 Å)/BCP (50 Å)/Alq3 (50 Å)/Li:Al (1500 Å).

Figure 1D:
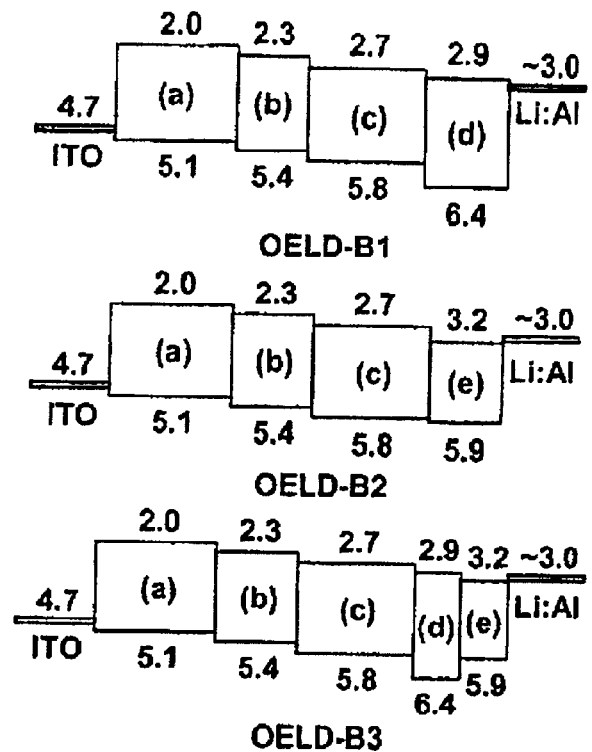
Figure 1E:
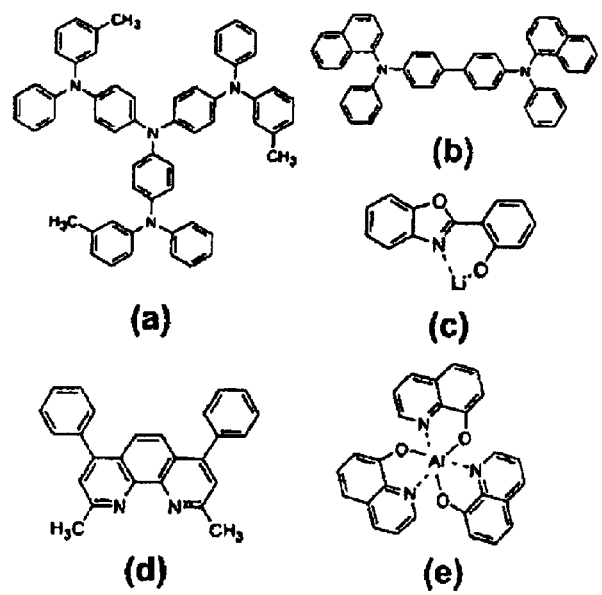

Energy band diagrams of the OELDs and chemical structures of the organic materials: (a) m-MTDATA, (b) NPB, (c) LiPBO, (d) BCP, and (e) Alq3 are shown in FIGS. 1d and 1e, respectively.

Figure 6:
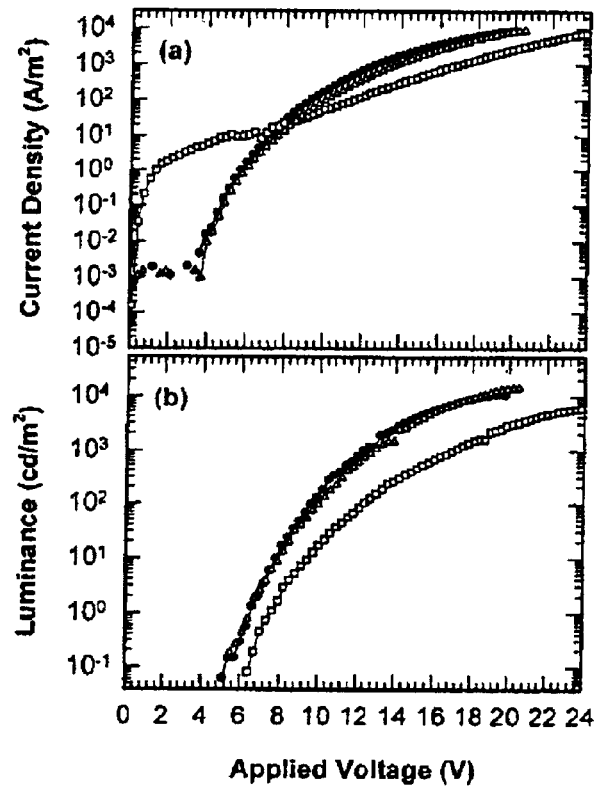
FIG. 6 demonstrates variations of the current density (A/m$^2$) and luminance (cd/m$^2$) of the electroluminescent devices obtained in Preparation 6 of the present invention as function of applied voltage(V)
Figure 7:
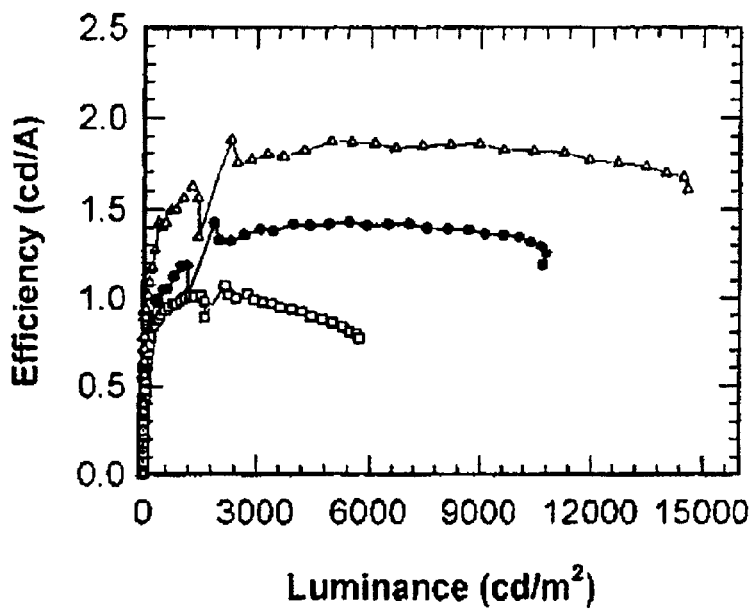
FIG. 7 depicts changes in the luminous efficiencies (cd/A) with luminance (cd/A) of the OELD-B1 (filled circle), OELD-B2 (open rectangle) and OELD-B3 (open triangle) obtained in Preparation 6.

The luminescence characteristics of the OELD-B1, OELD-B2 and OELD-B3 are shown in FIGS. 6 and 7.

EXAMPLE 3

CIE Color Coordinate of the OELD

Figure 5:
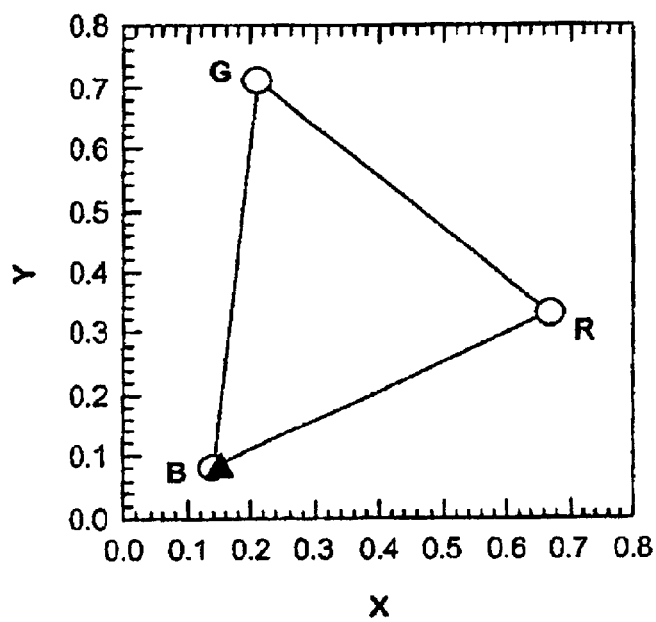
FIG. 5 shows CIE color coordinate of the blue OELD-B1 in a multi-layered structure.

The color purity of OELD-B1 was measured with the calibrated candela meter (Minolta CS1000) and shown in FIG. 5. As shown in FIG. 5, the CIE color coordinate of the blue OELD is x=0.15 and y=0.08 at above 10,000 cd/m², which is the nearest value to the NTSC standard value of X=0.14 and y=0.08. In FIG. 5, open circles denote the NTSC standard blue, green and red values.

EXAMPLE 4

Luminescence of OELD

FIG. 6 illustrates variations of the current density (A/m²) and luminance (cd/m²) of OELD-B1, OELD-B2 and OELD-B3 obtained in Preparation 6 as function of the applied voltage (V). For both OELD-B1 and OELD-B3, the current injection starts at ca. 3.5V. The maximum luminances of three OELDs are ca. 10,000 cd/m² or over, and in particular, ca. 14,600 cd/m², and 500 cd/m² can be achieved with OELD-B3 at 11V.

EXAMPLE 5

Efficiency of OELD

FIG. 7 depicts changes in the luminous efficiencies (cd/A) with luminance (cd/m²) of OELD-B1, OELD-B2 and OELD-B3, respectively. The luminous efficiency is steady at 1.2 lm/W at a current density of 200 A/m² and beyond.

As can be seen from the above results, the organometallic luminescent material of the present invention exhibits blue, green or red light emission. Therefore, an electroluminescent device containing the same is capable of exhibiting a full range of colors in the visible region with a high efficiency.

While the embodiments of the subject invention have been described and illustrated, it is obvious that various changes and modifications can be made therein without departing from the spirit of the present invention which should be limited only by the scope of the appended claims.

What is claimed is:

1. An organometallic luminescent material comprising a compound of formula (I):

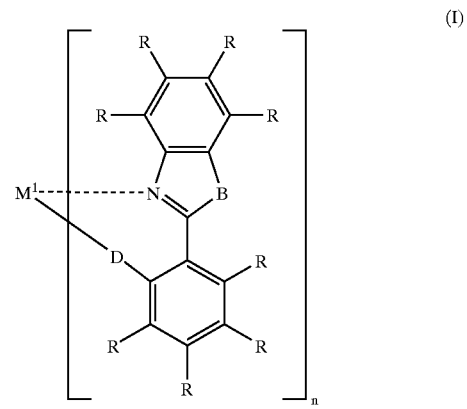

wherein,
M¹ is a monovalent or tetravalent metal selected from the group consisting of Li, Na, K, Zr, Si, Ti, Sn, Cs, Fr, Rb, Hf, Pr, Pa, Ge, Pb, Tm and Md;
R is hydrogen or $C_{1-10}$ alkyl;
B is O, S, Se or Te;
D is O or S; and
n is an integer ranging from 1 to 4.

2. An electroluminescent device which comprises an organic luminescent layer containing the organometallic luminescent material of claim 1.

3. The device of claim 2, wherein the organometallic luminescent material is present alone, or in combination with a polymer or an inorganic material, or in the form of a dopant in a polymer.

4. The device of claim 2 wherein the organic luminescent layer is formed by a spin coating, vapor deposition, vacuum thermal deposition, sputtering or electron beam deposition method.

5. An organometallic luminescent material of claim 1 wherein M¹ is a monovalent metal.

6. An organometallic luminescent material of claim 1 wherein M¹ is a tetravalent metal.

* * * * *